United States Patent
Ediebah et al.

(10) Patent No.: US 11,996,201 B2
(45) Date of Patent: May 28, 2024

(54) TECHNOLOGY TO AUTOMATICALLY IDENTIFY THE MOST RELEVANT HEALTH FAILURE RISK FACTORS

(71) Applicant: Abbott Laboratories, Abbott Park, IL (US)

(72) Inventors: Divine E. Ediebah, San Francisco, CA (US); Hajime Kusano, San Jose, CA (US); Ciaran A. Byrne, San Francisco, CA (US); Krishnankutty Sudhir, Santa Clara, CA (US); Nick West, Santa Clara, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 299 days.

(21) Appl. No.: 17/192,237

(22) Filed: Mar. 4, 2021

(65) Prior Publication Data
US 2022/0285028 A1 Sep. 8, 2022

(51) Int. Cl.
*G16H 50/30* (2018.01)
*G16H 50/20* (2018.01)

(52) U.S. Cl.
CPC .............. *G16H 50/30* (2018.01); *G16H 50/20* (2018.01)

(58) Field of Classification Search
CPC ........ G16H 50/30; G16H 50/20; G16H 10/16; G06N 20/00; G06N 5/04; G06F 16/2457; A61B 5/00; G16B 40/00

USPC .......................................................... 705/2, 3
See application file for complete search history.

(56) References Cited

U.S. PATENT DOCUMENTS

| | | | |
|---|---|---|---|
| 2011/0295622 A1 | 12/2011 | Farooq et al. | |
| 2014/0257122 A1* | 9/2014 | Ong | A61B 5/316 705/2 |
| 2019/0220975 A1 | 7/2019 | Hsieh et al. | |
| 2020/0005900 A1 | 1/2020 | Cha et al. | |
| 2020/0175418 A1* | 6/2020 | Pham | G06F 16/24573 |
| 2020/0205745 A1 | 7/2020 | Khosousi et al. | |
| 2022/0015714 A1* | 1/2022 | Hagar | A61B 5/7221 |

OTHER PUBLICATIONS

Shilaskar et al. "Feature selection for medical diagnosis: Evaluation for cardiovascular diseases", https://www.sciencedirect.com/science/article/pii/S0957417413000456 (Year: 2013).*
Dutta et al. "An Efficient Convolutional Neural Network for Coronary Heart Disease Prediction", https://www.sciencedirect.com/science/article/pii/S0957417420302323 (Year: 2020).*

(Continued)

*Primary Examiner* — Alaaeldin M Elshaer
(74) *Attorney, Agent, or Firm* — Foley & Lardner LLP

(57) ABSTRACT

Systems, apparatuses and methods may provide technology that identifies minority class data and majority class data in patient-level data, wherein the minority class data corresponds to patients with a health failure and the majority class data corresponds to patients without the health failure, oversamples the minority class data to obtain synthetic class data and automatically reduces, via a machine learning classifier, a set of risk factor variables based on the majority class data, the minority class data and the synthetic class data.

23 Claims, 9 Drawing Sheets

(56) References Cited

OTHER PUBLICATIONS

Chawla et al. "SMOTE: Synthetic Minority Over-sampling Technique", https://www.jair.org/index.php/jair/article/view/10302/24590 (Year: 2002).*

International Search Report and Written Opinion for Application No. PCT/US2022/018717, dated Jun. 17, 2022, 11 pages.

\* cited by examiner

| Patient 1 | |
|---|---|
| Health Failure | Y |
| Age | 65.7 |
| BMI | 30.5 |
| Diabetes | Y |
| ⋮ | |
| Procedure Duration | Y |
| ⋮ | |
| Ref. Vessel Diameter | 2.8 |
| ⋮ | |

| Patient 2 | |
|---|---|
| Health Failure | N |
| Age | 64.6 |
| BMI | - |
| Diabetes | - |
| ⋮ | |
| Baseline Diastolic | 77.3 |
| ⋮ | |
| Baseline Platelet Ct. | 230.9 |
| ⋮ | |

FIG. 1

TECHNOLOGY TO AUTOMATICALLY IDENTIFY THE MOST RELEVANT HEALTH FAILURE RISK FACTORS

TECHNICAL FIELD

Embodiments generally relate to automated risk failure analysis in healthcare settings. More particularly, embodiments relate to technology that automatically identifies the most relevant health failure risk factors.

BACKGROUND

Percutaneous coronary intervention (PCI, e.g., coronary angioplasty), is a nonsurgical procedure that improves blood flow to the heart. Target lesion failure (TLF) is a health failure (e.g., heart attack, cardiac death) related to the vessel targeted in a PCI. Current TLF risk prevention solutions are typically based on simple clinical parameters from relatively outdated studies and/or restricted population subsets. Accordingly, the solutions may fail to accurately capture the risk of future TLF events in patients.

SUMMARY

In accordance with one or more embodiments, a computing system comprises a processor and a memory coupled to the processor, the memory including a set of instructions, which when executed by the processor, cause the computing system to identify minority class data and majority class data in patient-level data, wherein the minority class data corresponds to patients with a health failure and the majority class data corresponds to patients without the health failure, oversample the minority class data to obtain synthetic class data, and automatically reduce, via a machine learning classifier, a set of risk factor variables based on the majority class data, the minority class data and the synthetic class data.

In accordance with one or more embodiments, at least one computer readable storage medium comprising a set of instructions, which when executed by a computing system, cause the computing system to identify minority class data and majority class data in patient-level data, wherein the minority class data corresponds to patients with a health failure and the majority class data corresponds to patients without the health failure, oversample the minority class data to obtain synthetic class data, and automatically reduce, via a machine learning classifier, a set of risk factor variables based on the majority class data, the minority class data and the synthetic class data.

In accordance with one or more embodiments, a method comprises identifying minority class data and majority class data in patient-level data, wherein the minority class data corresponds to patients with a health failure and the majority class data corresponds to patients without the health failure, oversampling the minority class data to obtain synthetic class data, and automatically reducing, via a machine learning classifier, a set of risk factor variables based on the majority class data, the minority class data and the synthetic class data.

BRIEF DESCRIPTION OF THE DRAWINGS

The various advantages of the embodiments will become apparent to one skilled in the art by reading the following specification and appended claims, and by referencing the following drawings, in which:

FIG. 1 is an illustration of an example of a portion of patient-level data according to an embodiment;

DESCRIPTION OF EMBODIMENTS

Turning now to FIG. 1, a portion of patient-level data 10 (10a, 10b) is shown in which various risk factor variables are captured for patients undergoing a medical procedure such as, for example, PCI. For example, a first data record 10a (e.g., for "Patient 1") documents that a health failure occurred (e.g., TLF within a given time frame such as four years) and other patient history information such as age, body mass index (BMI), diabetes condition, procedure duration, reference (e.g., target) vessel diameter, and so forth. Similarly, a second data record 10b (e.g., for "Patient 2") may document that the health failure did not occur and patient history information such as age, BMI, baseline diastolic blood pressure, baseline platelet count, and so forth.

The patient-level data 10 may generally be useful in predicting whether future patients will be considered high risk for the medical procedure. For example, the information collected for Patient 1 may be indicative of individuals considered to be high risk and the information collected for Patient 2 may be indicative of individuals considered to be low risk. Of particular note, however, is that the number of entries (e.g., data points) in the first data record 10a and the second data record 10b may be relatively high (e.g., dozens), depending on the health failure being tracked. Accordingly, collecting patient history information for all of the potential risk factors is typically not feasible in a typical healthcare setting. As will be discussed in greater detail, embodiments provide for removing imbalances in the patient-level data 10 and automatically reducing, via a machine learning (ML) classifier, the set of risk factor variables to a more manageable number that can be more readily handled in a typical healthcare setting. Additionally, although TLF is used to facilitate discussion in certain examples herein, the health failure may also be a bleeding event, a stent thrombosis, a treatment decision with an associated level of residual risk, a heart failure, etc., or any combination thereof.

Figure 2:
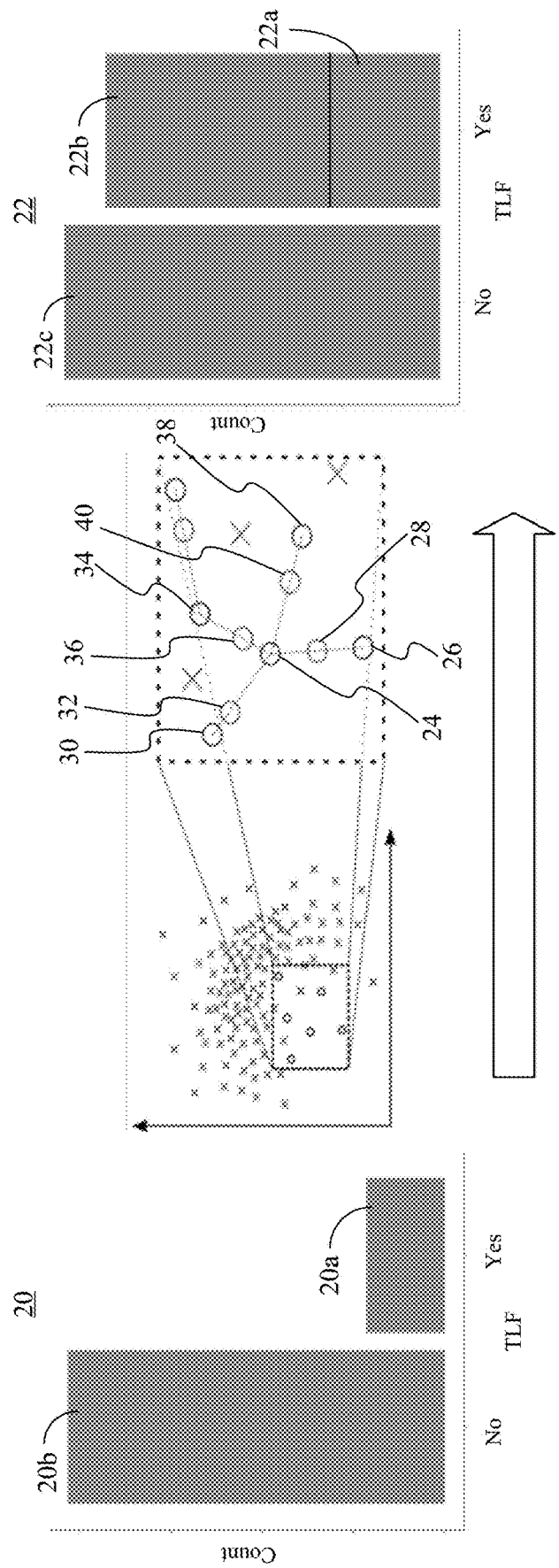
FIG. 2 is an illustration of an example of an oversampling of minority class data according to an embodiment.

Turning now to FIG. 2, a solution to handling data imbalances is shown. In the illustrated example, initial patient-level data 20 (20a, 20b) is partitioned into minority class data 20a and majority class data 20b. In an embodiment, the minority class data 20a corresponds to patients with a health failure (e.g., TLF Yes) and the majority class data 20b corresponds to patients without the health failure (e.g., TLF No). To render subsequent machine learning classifier techniques more effective, the minority class data 20a may be oversampled (e.g., using a synthetic minority oversampling technique/SMOTE, random oversampling, adaptive synthetic sampling/ADASYN, etc.). As a result, balanced patient-level data 22 (22a-22c) may include minority class data 22a, synthetic class data 22b (e.g., resulting from oversampling) and majority class data 22c. In the illustrated example, the sum of the minority class data 22a and the synthetic class data 22b is similar to the amount of the majority class data 22c, which enhances ML classifier performance.

More particularly, a first instance 24 and a second instance 26 (e.g., nearest neighbor) may be randomly sampled from the minority class data 20a, wherein a linear interpolation between the first instance 24 and the second instance 26 is conducted to obtain a synthetic instance 28. The interpolation may be for any risk factor variables that are shared by the first instance 24 and the second instance 26. Thus, if both instances 24, 26 include procedure duration information, the interpolation might involve distance-based averaging between the procedure duration values for the first instance 24 and the second instance 26. Similarly, the first instance 24 and a third instance 30 (e.g., nearest neighbor) may be randomly sampled from the minority class data 20a, with an interpolation being automatically conducted between the first instance 24 and the third instance 30 to obtain a synthetic instance 32. Additionally, a fourth instance 34 in the minority class data 20a may be used to generate a synthetic instance 36 and a fifth instance 38 in the minority class data 20a may be used to generate a synthetic instance 40.

Other data processing techniques may also be used such as, for example, removing outliers (e.g., using interquartile ranges), excluding variables with more than 20% missing data, imputing variables with less than 20% missing data (e.g., using multiple imputation by chain equation/MICE), and so forth. Additionally, standardizing/normalizing of the predictor variables may be used to enhance ML classifier performance. In one example, for variables with more than two levels, dummy variables are created. In an embodiment, variable selection is performed using embedded (e.g., based on an intrinsic model building metric) and wrapper (e.g., based on classifier performance) methods.

Figure 3:
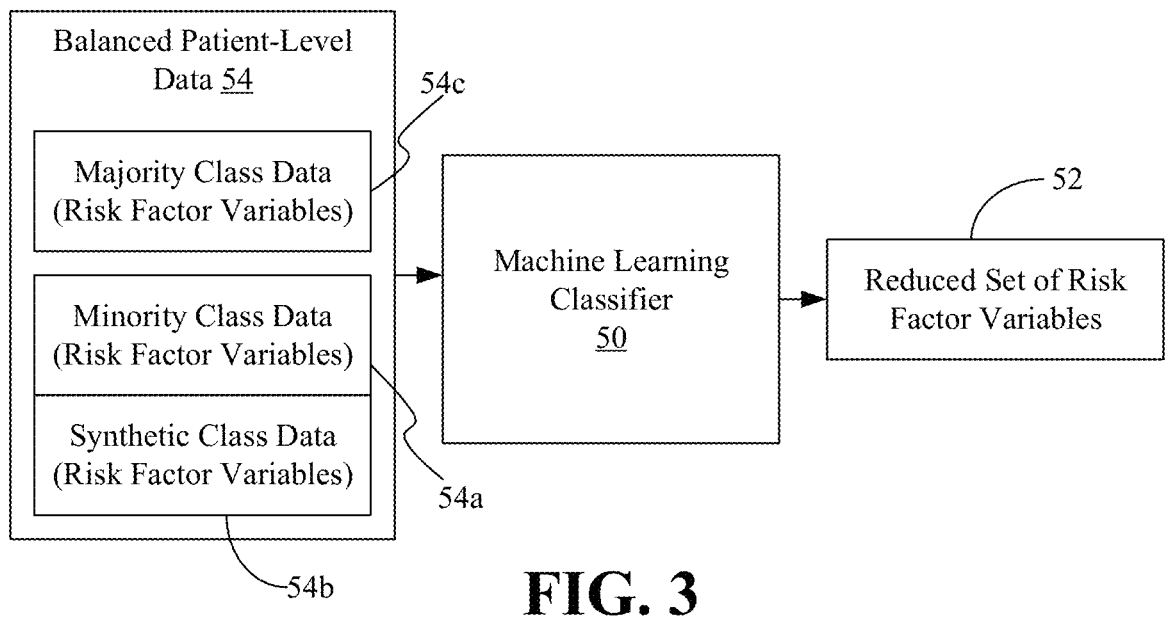
FIG. 3 is a block diagram of an example of an automatic reduction of risk factor variables according to an embodiment.

FIG. 3 shows a machine learning classifier 50 that may be used to extract a reduced set of risk factor variables 52 from balanced patient-level data 54 (54a-54c). In an embodiment, the balanced patient-level data 54 includes minority class data 54a, synthetic class data 54b and majority class data 54c. In the illustrated example, each of the classes includes data records with various risk factor variables, where the total set of risk factor variables may be too large to be used in a traditional healthcare setting. Accordingly, the illustrated machine learning classifier 50 is used (e.g., via Boruta feature selection as a wrapper built around Random Forest classification technology) to automatically reduce the total set of risk factor variables to the reduced set of risk factor variables 52.

The illustrated solution therefore aids in clinical decision making for both the patient and physician in that 1) the patient can be made aware of the risk of having the health failure if, for example the patient does not control their blood pressure level and/or glucose level by exercising or medication, 2) the physician may not need to collect as much patient data or procedure data to provide informed clinical advice to the patient, 3) with respect to monitoring patients identified as being high risk of the health failure, appropriate measures may be taken to mitigate the health failure by either more frequent hospital visits as opposed to those patients identified to have low risk, 4) physicians may mitigate higher risk of the health failure. Embodiments provide a tool that can easily be used by clinicians/physicians rapidly. Indeed, it may take only a few minutes to plug in data for a relatively small set (e.g., 6 to 10 variables) to obtain a patient risk score.

Figure 4A:
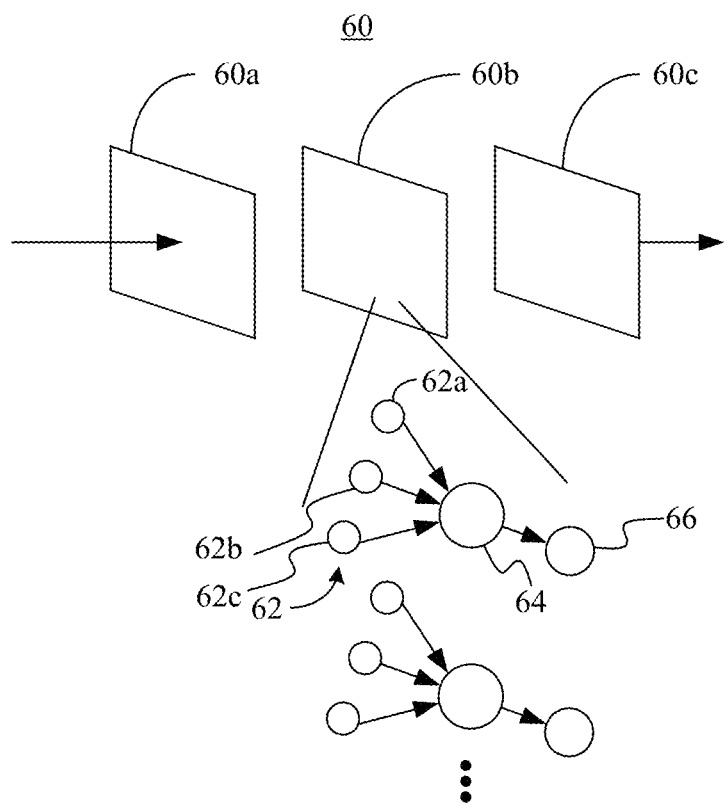
FIG. 4A is an illustration of an example of a multi-layer neural network according to an embodiment.

FIG. 4A shows a multi-layer neural network 60 (60a-60c) that may be readily incorporated into the machine learning classifier 50 (FIG. 3), already discussed. The network 60 may generally include an input layer 60a, an output layer 60c and one or more hidden/intermediate layers 60b. To train the neural network 60, a portion (e.g., 75%) of balanced patient-level data may be used as inputs for one or more forward propagations (e.g., forward passes moving from input to output), which computes a gradient of a loss function with respect to current weights. For example, a set of inputs 62 (62a-62b) to a neuron 64 may be weighted (e.g., via synapses) to provide an output value 66. Thus, a first input 62a may correspond to a first risk factor variable (e.g., age) having a first weight, a second input 62b might correspond to a second risk factor variable (e.g., BMI) having a second weight and a third input 62c may correspond to a third risk factor variable (e.g., procedure duration) having a third weight. In an embodiment, the output value 66 may be continuous, binary or categorical.

Additionally, one or more backward propagations (e.g., backward passes moving from output to input) may use the measured output and the actual output to update the current weights in a manner that reduces the value of the loss function. In one example, the forward and backward propagations are conducted iteratively until the loss function converges to an acceptably low value. The result of the training may therefore provide weighted risk factor variables that enable the most relevant risk factor variables to be selected as a reduced set of risk factor variables. As will be discussed in greater detail, the remaining portion (e.g., 25%) of the balanced patient-level data may be used to confirm the effectiveness of the neural network in drawing real-time inferences using only the most relevant risk factor variables.

Figure 4B:
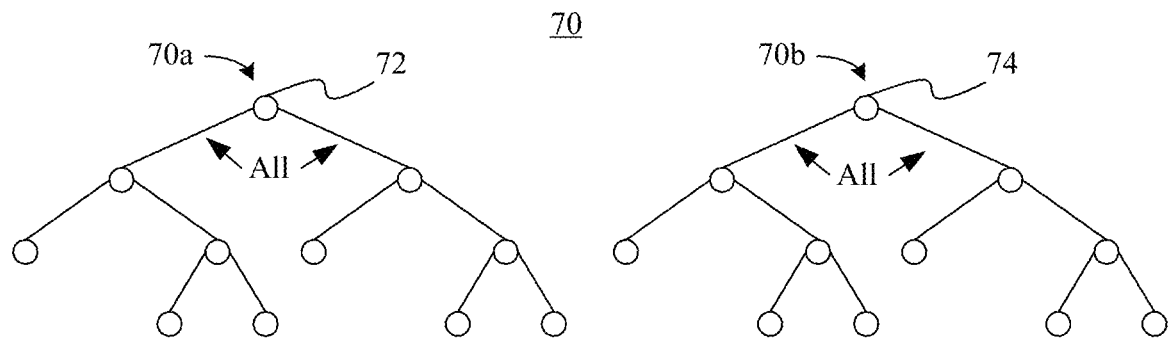
FIG. 4B is an illustration of an example of a Random Forest classifier according to an embodiment.

FIG. 4B shows a Random Tree classifier 70 (70a, 70b) that may be readily incorporated into the machine learning classifier 50 (FIG. 3), already discussed. In general, the Random Tree classifier 70 may include a series of yes/no questions asked about the patient-level data that eventually lead to a predicted class (e.g., TLF Yes, TLF No). More particularly, the classifier 70 may randomly sample training data points when building decision trees and consider random subsets of variables when splitting nodes. In the illustrated example, a first decision tree 70a begins with a first node 72 corresponding to a split decision about a risk factor variable (e.g., is age greater than 65 years). Similarly, a second decision tree 70b may begin with a second node 74 corresponding to a split decision about another risk factor variable (e.g., is total stent length greater than 30 millimeters). While two trees 70a, 70b are shown to facilitate discussion, the classifier 70 might include hundreds or thousands of decision trees. In an embodiment, the Random Tree classifier 70 tests all possible splits over a fraction of the variables. The final predictions of the classifier 70 may be made by averaging the predictions of each individual tree 70a, 70b.

Figure 4C:
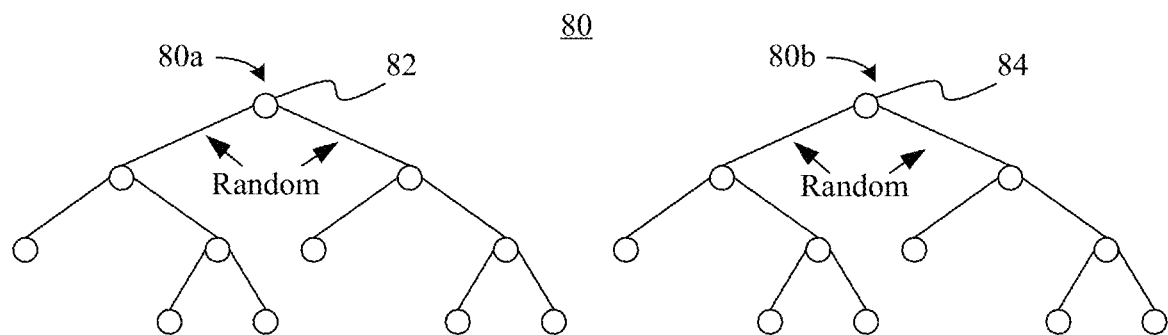
FIG. 4C is an illustration of an example of an Extra Trees classifier according to an embodiment.

FIG. 4C shows an Extra Trees classifier 80 (80a, 80b) that may be readily incorporated into the machine learning classifier 50 (FIG. 3), already discussed. In general, the Extra Trees classifier 80 may include a series of yes/no questions asked about the patient-level data that eventually lead to a predicted class (e.g., TLF Yes, TLF No). More particularly, the classifier 80 may randomly sample training data points when building decision trees and consider random subsets of variables when splitting nodes. In the illustrated example, a first decision tree 80a begins with a first node 82 corresponding to a split decision about a risk factor variable (e.g., is baseline diastolic blood pressure less than 77 mmHg). Similarly, a second decision tree 80b may begin with a second node 84 corresponding to a split decision about another risk factor variable (e.g., is baseline systolic blood pressure less than 141 mmHg). Again, while two trees 80a, 80b are shown to facilitate discussion, the classifier 80 might include hundreds or thousands of decision trees. In an embodiment, the Extra Trees classifier 80 tests random splits over a fraction of the variables as opposed to all splits as in the Random Tree classifier 70 (FIG. 4B), already discussed. The final predictions of the classifier 80 may be made by averaging the predictions of each individual tree 80a, 80b.

Figure 5:
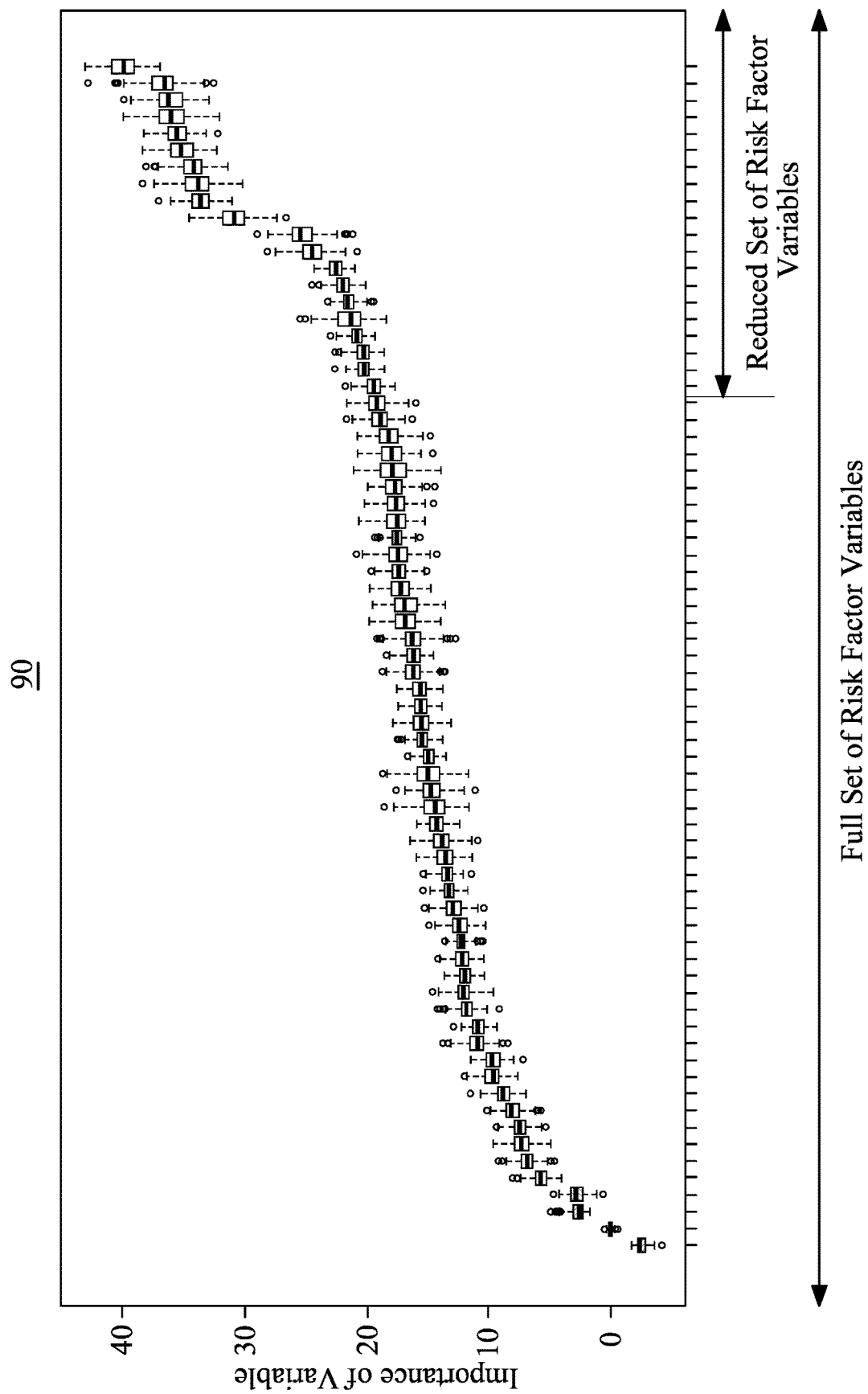
FIG. 5 is a plot of an example of a set of risk factor variables according to an embodiment.

Turning now to FIG. 5, a plot 90 demonstrates that the machine learning classifier may enable the risk factor variables to be automatically ranked in terms of importance. In the illustrated example, the reduced set of risk factor variables is substantially less than the full set of risk factor variables. With specific regard to TLF, the most relevant risk factor variables were reduced from over eighty variables to the following six variables: total stent length, procedure duration, baseline fasting blood glucose (FBG), diastolic blood pressure (BP), systolic blood pressure and baseline platelet count, with the results shown in Table I below.

TABLE I

| Model | Accuracy | Specificity | Sensitivity |
| --- | --- | --- | --- |
| Logistic Regression | 56% | 76% | 35% |
| Random Forest Classifier | 81% | 85% | 77% |
| Extra Tree Classifier | 83% | 82% | 82% |
| Multi-Layer Neural Network | 75% | 77% | 72% |

Thus, the Extra Tree classifier performed the best in terms of sensitivity (e.g., recall, capturing the true event of TLF Yes). All of the machine learning classifiers performed substantially better than logistic regression (e.g., multivariable logistic regression/MVLR). To evaluate ML classifiers, a confusion matrix may be used to calculate sensitivity, specificity, precision, recall, F1 score, etc., as shown in Table II below.

TABLE II

| Metric | Formula | Interpretation |
| --- | --- | --- |
| Accuracy | $\frac{TP + TN}{TP + TN + FP + FN}$ | Overall performance of model |
| Precision | $\frac{TP}{TP + FP}$ | How accurate the positive predictions are |
| Recall/Sensitivity | $\frac{TP}{TP + FN}$ | Coverage of actual positive sample |
| Specificity | $\frac{TN}{TN + FP}$ | Coverage of actual negative sample |
| F1 score | $\frac{2TP}{2TP + FP + FN}$ | Hybrid metric useful for unbalanced data |

Figure 6:
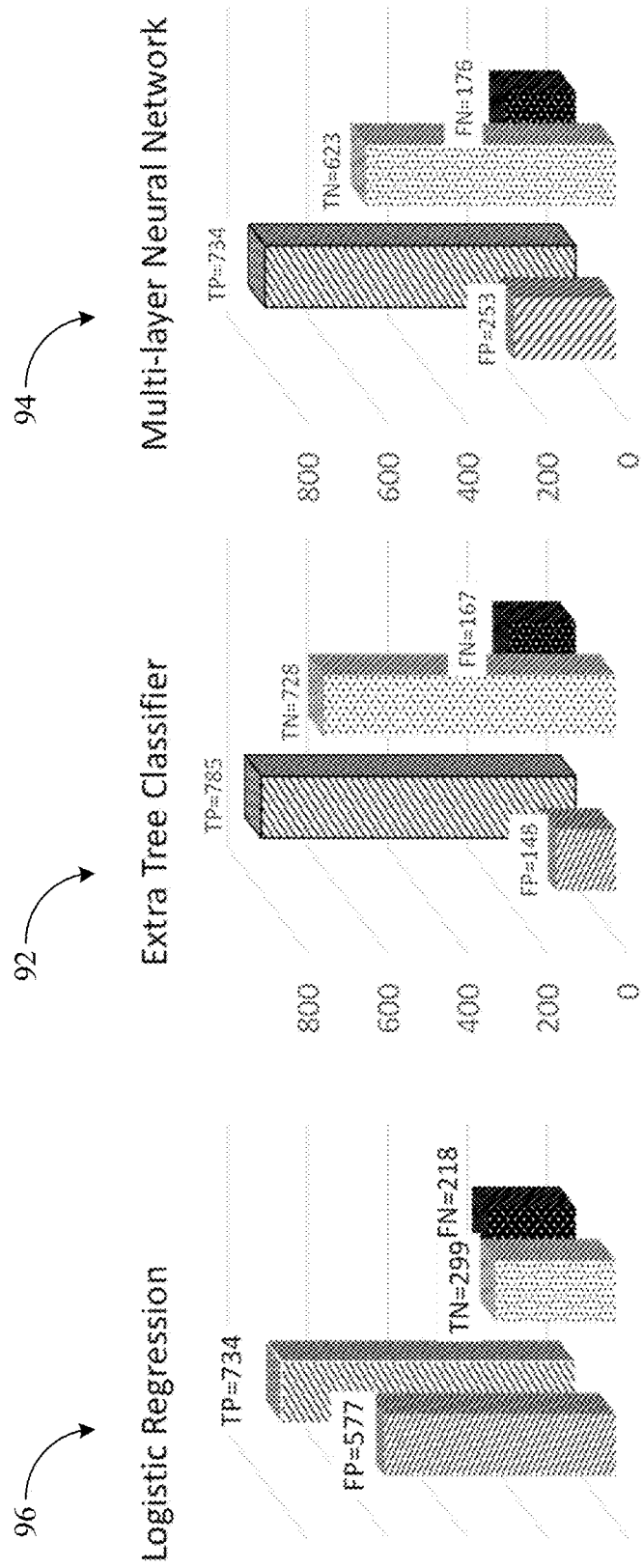
FIG. 6 is a plot of example results according to an embodiment.

To interpret ML models, Shapely values may be used as shown in FIG. 6 (e.g., assuming that each feature value of the instance is a "player" in a game where the prediction is the payout). In the illustrated example, an Extra Tree Classifier result 92 is more advantageous (e.g., has a higher payout) than a Multi-Layer Neural Network result 94 and a Logistic Regression result 96.

Figure 7A:
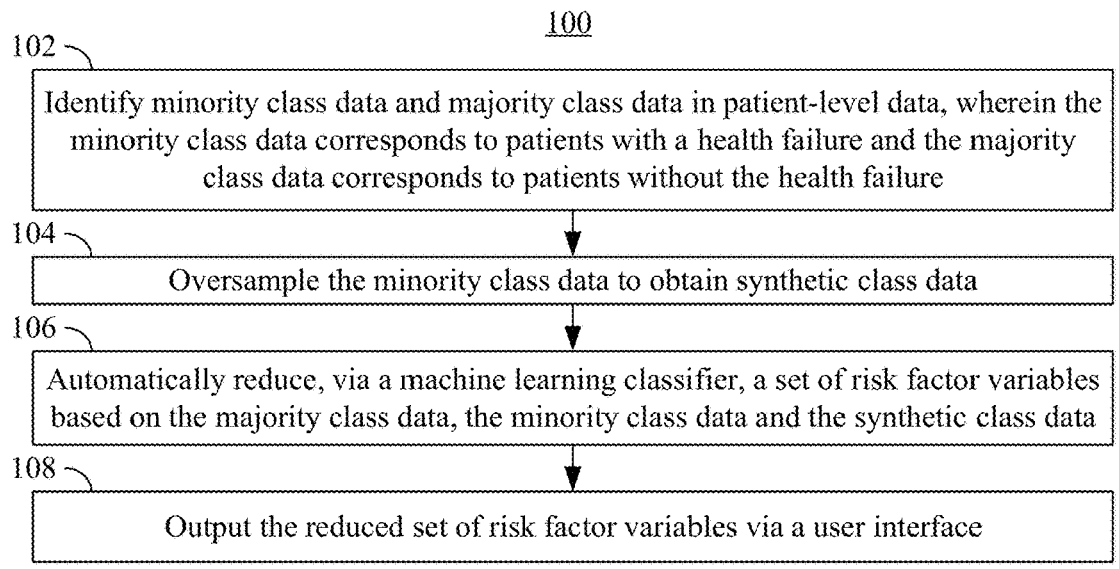
FIG. 7A is a flowchart of an example of a method of operating a performance-enhanced computing system according to an embodiment.

FIG. 7A shows a method 100 of operating a performance-enhanced computing system. The method 100 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

Illustrated processing block 102 provides for identifying minority class data and majority class data in patient-level data, wherein the minority class data corresponds to patients with a health failure and the majority class data corresponds to patients without the health failure. Block 102 may include automatically parsing the patient-level data to identify health failure information on a per patient basis. In an embodiment, block 104 oversamples the minority class data to obtain synthetic class data. Additionally, block 106 automatically reduces, via a machine learning classifier, a set of risk factor variables based on the majority class data, the minority class data and the synthetic class data. Block 106 may include using a multi-layer neural network, an Extra Trees classifier and/or a Random Forest classifier, as already discussed. The reduced set of risk factor variables is output via a user interface (e.g., display, speaker) at block 108.

In one example, the health failure is a TLF, although other health failures/outcomes such as, for example, bleeding events, stent thromboses and/or heart failures, may also be analyzed. The health failure may also be a treatment decision (e.g., medication) with an associated level of residual risk. In the case of TLF, the reduced set of risk factor variables may be total stent length, procedure duration, baseline fasting blood glucose, diastolic blood pressure, systolic blood pressure and baseline platelet count. Other risk factor variables such as optical coherence tomography (OCT) and/or fractional flow reserve (FFR), may also be considered.

The illustrated method 100 therefore enhances performance at least to the extent that the reduced set of risk factor variables enables the patient to be made aware of the risk of having the health failure if, for example the patient does not control their blood pressure level and/or glucose level by exercising or medication. The reduced set of risk factor variables also enables the physician to collect less patient data or procedure data to provide informed clinical advice to the patient. Additionally, the reduced set of risk factor variables enables appropriate measures to be taken to mitigate the health failure by either more frequent hospital visits as opposed to those patients identified to have low risk. Moreover, the reduced set of risk factor variables enables physicians to mitigate higher risk of the health failure.

Figure 7B:
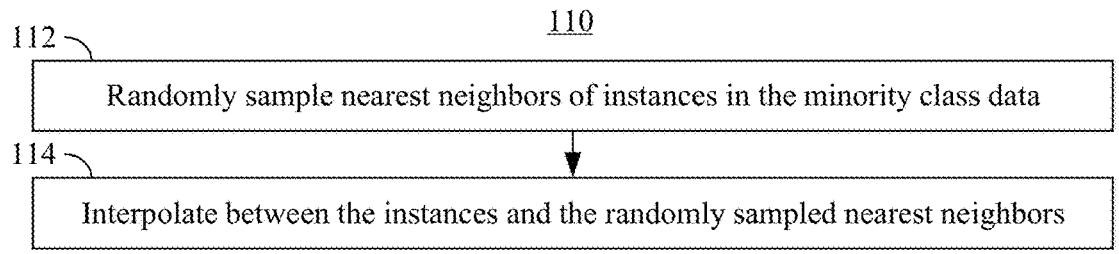
FIG. 7B is a flowchart of an example of a method of oversampling minority class data according to an embodiment.

FIG. 7B shows a method 110 of oversampling minority class data. The method 110 may generally be incorporated into block 104 (FIG. 7A), already discussed. More particularly, the method 110 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof.

Illustrated processing block 112 provides for randomly sampling nearest neighbors of instances in the minority class data. In an embodiment, block 114 interpolates between the instances and the randomly sampled nearest neighbors. For example, block 114 might involve distance-based averaging between the risk factor values for each instance and corresponding nearest neighbor. The method 110 therefore further enhances performance by balancing the patient-level data.

Figure 8:
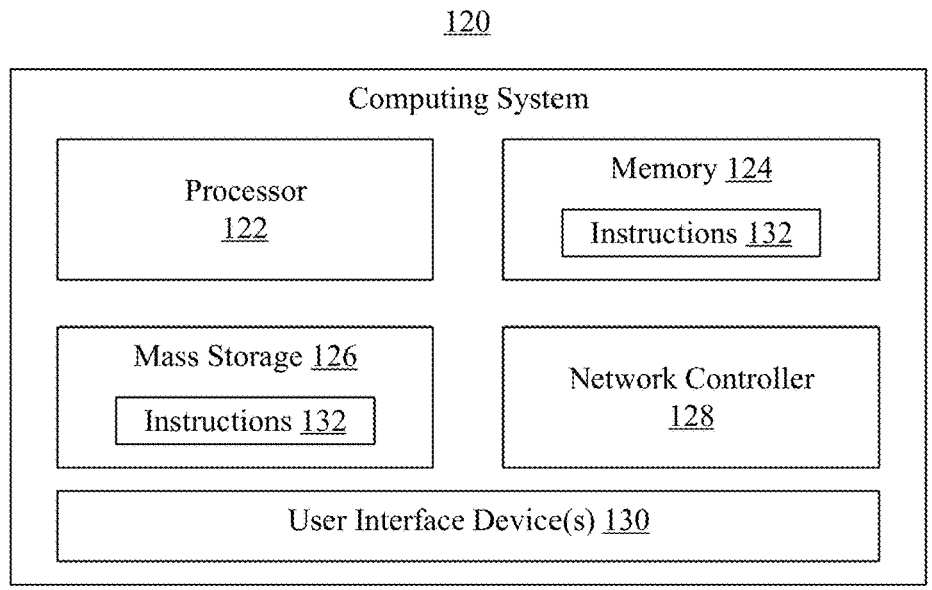
FIG. 8 is a block diagram of an example of a computing system according to an embodiment.

Turning now to FIG. 8, a performance-enhanced computing system 120 is shown. In the illustrated example, the computing system 120 includes a processor 122, a memory 124 (e.g., volatile memory such as, for example, DRAM), mass storage 126 (e.g., persistent or non-volatile memory such as, for example, ROM, flash memory, solid state drive/SSD, hard disk drive/HDD), a network controller 128 (e.g., wired and/or wireless) and one or more user interface devices 130 (e.g., display, speaker). In an embodiment, the memory 124 and/or the mass storage 126 include a set of instructions 132, which when executed by the processor 122, cause the processor 122 and/or the computing system 120 to perform one or more aspects of the method 100 (FIG. 7A) and/or the method 110 (FIG. 7B), already discussed.

Thus, execution of the instructions 132 may cause the processor 122 and/or the computing system 120 to identify minority class data and majority class data in patient-level data, wherein the minority class data corresponds to patients without a health failure and the majority class data corresponds to patients without the health failure. Execution of the instructions 132 may also cause the processor 122 and/or the computing system 120 to oversample the minority class data to obtain synthetic class data and automatically reduce, via a machine learning classifier, a set of risk factor variables based on the majority class data, the minority class data and the synthetic class data. In an embodiment, the instructions, when executed, further cause the processor 122 and/or the computing system 120 to output the reduced set of risk factor variables via the user interface device(s) 130.

The computing system 120 is therefore considered performance enhanced at least to the extent that the computing system 120 enables better healthcare outcomes. For example, the reduced set of risk factor variables enables the patient to be made aware of the risk of having the health failure if, for example the patient does not control their blood pressure level and/or glucose level by exercising or medication. The reduced set of risk factor variables also enables the physician to collect less patient data or procedure data to provide informed clinical advice to the patient. Additionally, the reduced set of risk factor variables enables appropriate measures to be taken to mitigate the health failure by either more frequent hospital visits as opposed to those patients identified to have low risk. Moreover, the reduced set of risk factor variables enables physicians to mitigate higher risk of the health failure.

Figure 9A:
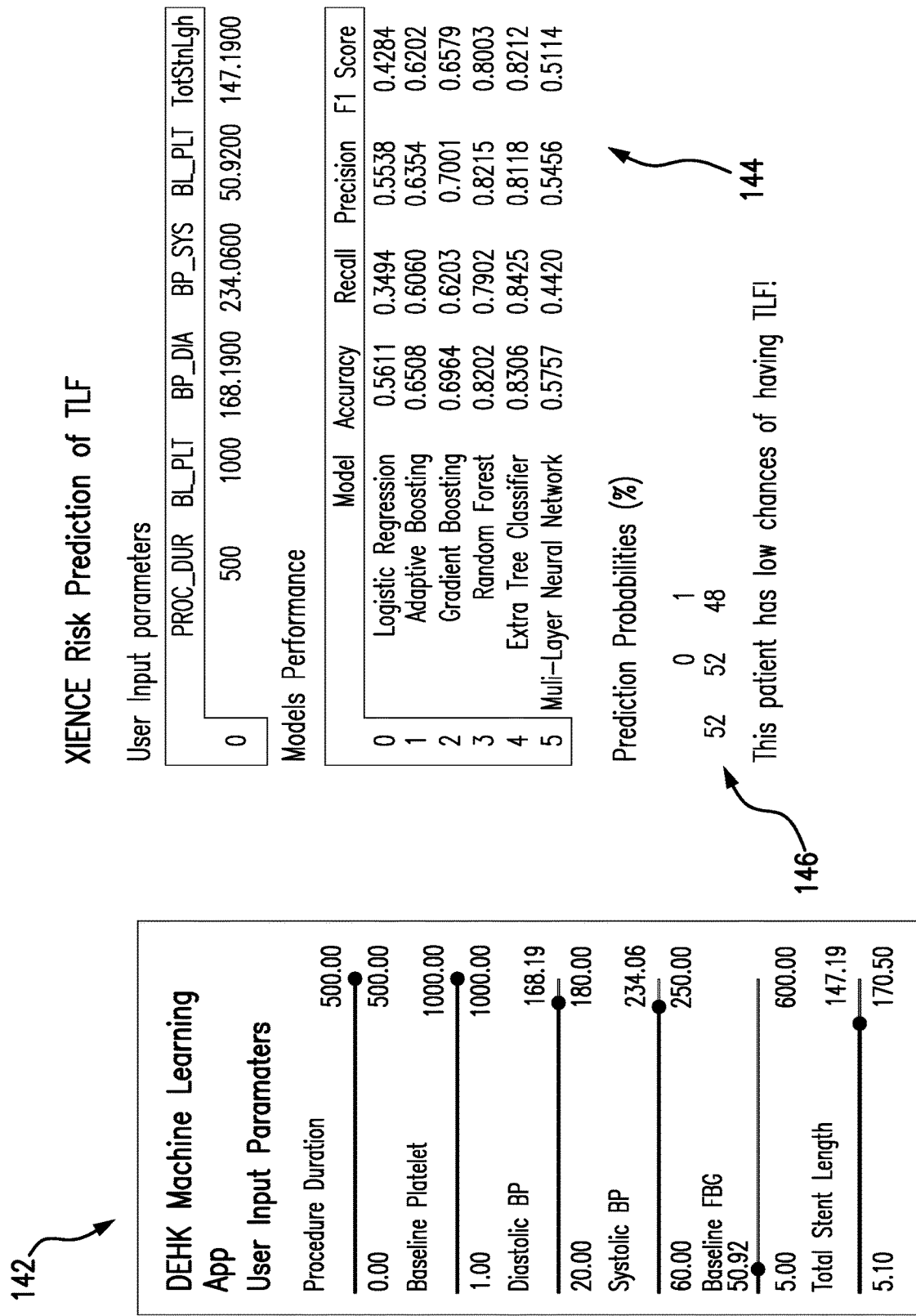
FIG. 9A is an illustration of a risk prediction interface according to an embodiment.

Turning now to FIG. 9A, a risk prediction interface 140 is shown that may be presented to a user (e.g., medical professional) via a user interface device such as, for example, the user interface device(s) 130, already discussed. In the illustrated example, a "DEHK" (Divine Ediebah Hajime Kusano) machine learning application 142 enables the user to enter user input parameter values (e.g., a reduced set of risk factor variable data corresponding to a patient receiving a XIENCE drug-eluting stent). In an embodiment, model performance data 144 indicates the accuracy, recall, precision and F1 score for various statistical models and machine learning classifiers (e.g., with the Random Forest classifier providing the highest precision). The risk prediction interface 140 may also include a prediction probability indicator 146 that specifies whether the patient is likely to encounter a health failure (e.g., TLF). In the illustrated example, the patient has a relatively low chance (48%) of having TLF.

Figure 9B:
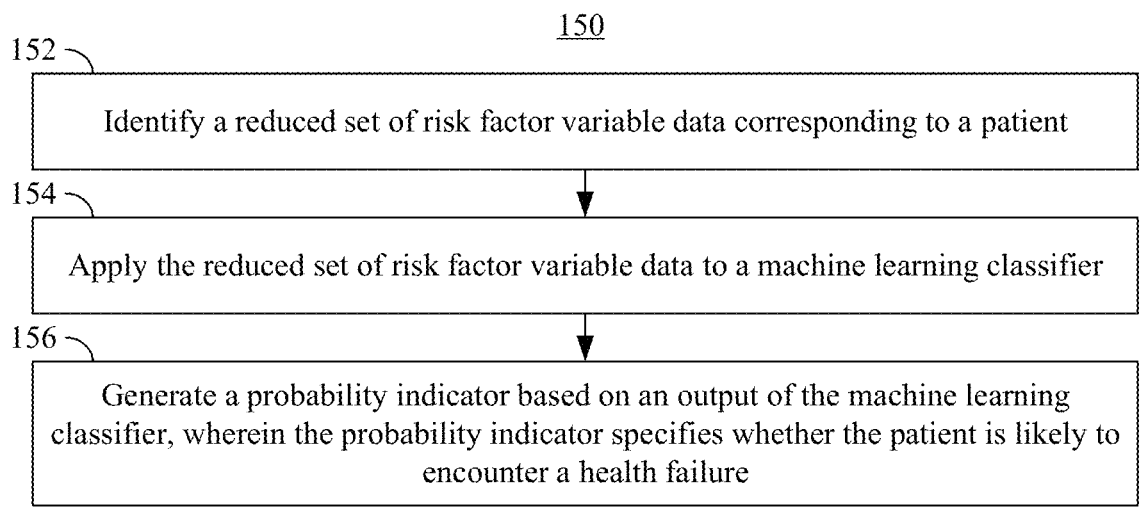
FIG. 9B is a flowchart of an example of a method of predicting risk based on a reduced set of risk factor variables according to an embodiment.

FIG. 9B shows a method 150 of generating a risk prediction interface such as, for example, the risk prediction interface 140 (FIG. 9A), already discussed. The method 150 may generally be implemented in a computing system such as, for example, the computing system 120 (FIG. 8), already discussed. More particularly, the method 150 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof.

Illustrated processing block 152 identifies a reduced set of risk factor variable data corresponding to a patient, wherein the reduced set of risk factor variable data is applied to a machine learning classifier (e.g., multi-layer neural network, Extra Trees classifier, Random Forest classifier) at block 154. In an embodiment, block 156 generates a probability indicator based on an output of the machine learning classifier. The probability indicator may specify whether the patient is likely to encounter a health failure (e.g., TLF, bleeding event, etc.). The illustrated method 150 therefore enables medical professionals to determine health failure risks without collecting large amounts of patient data.

ADDITIONAL NOTES AND EXAMPLES

Example 1 includes a computing system comprising a processor, and a memory coupled to the processor, the memory including a set of instructions, which when executed by the processor, cause the computing system to identify minority class data and majority class data in patient-level data, wherein the minority class data corresponds to patients with a health failure and the majority class data corresponds to patients without the health failure, oversample the minority class data to obtain synthetic class data, and automatically reduce, via a machine learning classifier, a set of risk factor variables based on the majority class data, the minority class data and the synthetic class data.

Example 2 includes the computing system of Example 1, wherein to oversample the minority class data, the instructions, when executed, cause the computing system to randomly sample nearest neighbors of instances in the minority class data, and interpolate between the instances and the randomly sampled nearest neighbors.

Example 3 includes the computing system of Example 1, wherein the machine learning classifier is a multi-layer neural network.

Example 4 includes the computing system of Example 1, wherein the machine learning classifier is an Extra Trees classifier.

Example 5 includes the computing system of Example 1, wherein the machine learning classifier is a Random Forest classifier.

Example 6 includes the computing system of Example 1, wherein the health failure is one or more of a target lesion failure, a bleeding event, a stent thrombosis, a treatment decision with an associated level of residual risk or a heart failure.

Example 7 includes the computing system of Example 6, wherein the reduced set of risk factor variables is selected from a group consisting of total stent length, procedure duration, baseline fasting blood glucose, diastolic blood pressure, systolic blood pressure and baseline platelet count.

Example 8 includes the computing system of Example 1, wherein the instructions, when executed, further cause the computing system to output the reduced set of risk factor variables via a user interface.

Example 9 includes at least one computer readable storage medium comprising a set of instructions, which when executed by a computing system, cause the computing system to identify minority class data and majority class data in patient-level data, wherein the minority class data corresponds to patients with a health failure and the majority class data corresponds to patients without the health failure, oversample the minority class data to obtain synthetic class data, and automatically reduce, via a machine learning classifier, a set of risk factor variables based on the majority class data, the minority class data and the synthetic class data.

Example 10 includes the at least one computer readable storage medium of Example 9, wherein to oversample the minority class data, the instructions, when executed, cause the computing system to randomly sample nearest neighbors of instances in the minority class data, and interpolate between the instances and the randomly sampled nearest neighbors.

Example 11 includes the at least one computer readable storage medium of Example 9, wherein the machine learning classifier is a multi-layer neural network.

Example 12 includes the at least one computer readable storage medium of Example 9, wherein the machine learning classifier is an Extra Trees classifier.

Example 13 includes the at least one computer readable storage medium of Example 9, wherein the machine learning classifier is a Random Forest classifier.

Example 14 includes the at least one computer readable storage medium of Example 9, wherein the health failure is one or more of a target lesion failure, a bleeding event, a stent thrombosis, a treatment decision with an associated level of residual risk or a heart failure.

Example 15 includes the at least one computer readable storage medium of Example 14, wherein the reduced set of risk factor variables is selected from a group consisting of total stent length, procedure duration, baseline fasting blood glucose, diastolic blood pressure, systolic blood pressure and baseline platelet count.

Example 16 includes the at least one computer readable storage medium of Example 9, wherein the instructions, when executed, further cause the computing system to output the reduced set of risk factor variables via a user interface.

Example 17 includes a method comprising identifying minority class data and majority class data in patient-level data, wherein the minority class data corresponds to patients with a health failure and the majority class data corresponds to patients without the health failure, oversampling the minority class data to obtain synthetic class data, and automatically reducing, via a machine learning classifier, a set of risk factor variables based on the majority class data, the minority class data and the synthetic class data.

Example 18 includes the method of Example 17, wherein oversampling the minority class data includes randomly sampling nearest neighbors of instances in the minority class data, and interpolating between the instances and the randomly sampled nearest neighbors.

Example 19 includes the method of Example 17, wherein the machine learning classifier is a multi-layer neural network.

Example 20 includes the method of Example 17, wherein the machine learning classifier is an Extra Trees classifier.

Example 21 includes the method of Example 17, wherein the machine learning classifier is a Random Forest classifier.

Example 22 includes the method of Example 17, wherein the health failure is one or more of a target lesion failure, a bleeding event, a stent thrombosis, a treatment decision with an associated level of residual risk or a heart failure.

Example 23 includes the method of Example 22, wherein the reduced set of risk factor variables is selected from a group consisting of total stent length, procedure duration, baseline fasting blood glucose, diastolic blood pressure, systolic blood pressure and baseline platelet count.

Example 24 includes the method of Example 17, further including outputting the reduced set of risk factor variables via a user interface.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD (solid state drive)/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A; B; C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A computing system comprising:
    a processor; and
    a memory coupled to the processor, the memory including a set of instructions, which when executed by the processor, cause the computing system to:
        identify minority class data and majority class data in patient-level data, wherein the minority class data corresponds to patients with a health failure and the majority class data corresponds to patients without the health failure;
        oversample the minority class data to obtain synthetic class data; and
        automatically reduce, via a machine learning classifier, risk factor variables to a reduced set of risk factor variables based on the majority class data, the minority class data and the synthetic class data, wherein the machine learning classifier includes a multi-layer neural network configured to be trained using at least a portion of the patient-level data to perform one or more forward propagations and one or more rearward propagations until a value of a loss function is acceptable.

2. The computing system of claim 1, wherein to oversample the minority class data, the instructions, when executed, cause the computing system to:
    randomly sample nearest neighbors of instances in the minority class data; and
    interpolate between the instances and the randomly sampled nearest neighbors.

3. The computing system of claim 1, wherein the machine learning classifier includes an Extra Trees classifier configured to be trained by randomly sampling training data points when building a plurality of decision trees, considering random subsets of variables when splitting nodes of the plurality of decision trees, and testing random splits over a fraction of the variables.

4. The computing system of claim 1, wherein the machine learning classifier includes a Random Forest classifier configured to be trained by randomly sampling training data points when building a plurality of decision trees, considering random subsets of variables when splitting nodes of the plurality of decision trees, and testing all possible splits over a fraction of the variables.

5. The computing system of claim 1, wherein the health failure is one or more of a target lesion failure, a bleeding event, a stent thrombosis, a treatment decision with an associated level of residual risk or a heart failure.

6. The computing system of claim 5, wherein the reduced set of risk factor variables is selected from a group consisting of total stent length, procedure duration, baseline fasting blood glucose, diastolic blood pressure, systolic blood pressure and baseline platelet count.

7. The computing system of claim 1, wherein the instructions, when executed, further cause the computing system to provide one or more graphical user interfaces for display via a user interface, the one or more graphical user interfaces including two or more of:
    a user input section that facilitates entry of parameter values associated with a patient for each risk factor variable of the reduced set of risk factor variables for evaluation by the machine learning classifier;
    a model performance section that indicates performance characteristics of the machine learning classifier in evaluating the parameter values; or
    a prediction probability section that provides a prediction probability indicator that indicates whether the patient is likely to encounter the health failure based on the evaluation by the machine learning classifier.

8. A computing system comprising:
    a processor; and
    a memory coupled to the processor, the memory including a set of instructions, which when executed by the processor, cause the computing system to:
        identify minority class data and majority class data in patient-level data, wherein the minority class data corresponds to patients with a health failure and the majority class data corresponds to patients without the health failure;
        oversample the minority class data to obtain synthetic class data;
        automatically reduce, via a machine learning classifier, risk factor variables to a reduced set of risk factor variables based on the majority class data, the minority class data and the synthetic class data, wherein the machine learning classifier includes an Extra Trees classifier configured to be trained by randomly sampling training data points when building a plurality of decision trees, considering random subsets of variables when splitting nodes of the plurality of decision trees, and testing random splits over a fraction of the variables.

9. The computing system of claim 8, wherein to oversample the minority class data, the instructions, when executed, cause the computing system to:
    randomly sample nearest neighbors of instances in the minority class data; and interpolate between the instances and the randomly sampled nearest neighbors.

10. The computing system of claim 8, wherein the machine learning classifier includes a multi-layer neural network configured to be trained using at least a portion of the patient-level data to perform one or more forward propagations and one or more rearward propagations until a value of a loss function is acceptable.

11. The computing system of claim 8, wherein the plurality of decisions trees is a first plurality of decision trees, and wherein the machine learning classifier includes a Random Forest classifier configured to be trained by randomly sampling training data points when building a second plurality of decision trees, considering random subsets of variables when splitting nodes of the second plurality of decision trees, and testing all possible splits over a fraction of the variables.

12. The computing system of claim 8, wherein the health failure is one or more of a target lesion failure, a bleeding event, a stent thrombosis, a treatment decision with an associated level of residual risk or a heart failure.

13. The computing system of claim 12, wherein the reduced set of risk factor variables is selected from a group consisting of total stent length, procedure duration, baseline fasting blood glucose, diastolic blood pressure, systolic blood pressure and baseline platelet count.

14. The computing system of claim 8, wherein the instructions, when executed, further cause the computing system to provide one or more graphical user interfaces for display via a user interface, the one or more graphical user interfaces including two or more of:
a user input section that facilitates entry of parameter values associated with a patient for each risk factor variable of the reduced set of risk factor variables for evaluation by the machine learning classifier;
a model performance section that indicates performance characteristics of the machine learning classifier in evaluating the parameter values; or
a prediction probability section that provides a prediction probability indicator that indicates whether the patient is likely to encounter the health failure based on the evaluation by the machine learning classifier.

15. A method comprising:
identifying minority class data and majority class data in patient-level data, wherein the minority class data corresponds to patients with a health failure and the majority class data corresponds to patients without the health failure;
oversampling the minority class data to obtain synthetic class data; and
automatically reducing, via a machine learning classifier, risk factor variables to a reduced set of risk factor variables based on the majority class data, the minority class data and the synthetic class data, wherein the machine learning classifier includes a multi-layer neural network configured to be trained using at least a portion of the patient-level data to perform one or more forward propagations and one or more rearward propagations until a value of a loss function is acceptable.

16. The method of claim 15, wherein oversampling the minority class data includes:
randomly sampling nearest neighbors of instances in the minority class data; and
interpolating between the instances and the randomly sampled nearest neighbors.

17. The method of claim 15, wherein the health failure is one or more of a target lesion failure, a bleeding event, a stent thrombosis, a treatment decision with an associated level of residual risk or a heart failure.

18. The method of claim 17, wherein the reduced set of risk factor variables is selected from a group consisting of total stent length, procedure duration, baseline fasting blood glucose, diastolic blood pressure, systolic blood pressure and baseline platelet count.

19. The method of claim 15, further comprising outputting the reduced set of risk factor variables via a user interface.

20. The method of claim 15, further comprising providing one or more graphical user interfaces for display via a user interface, the one or more graphical user interfaces including two or more of:
a user input section that facilitates entry of parameter values associated with a patient for each risk factor variable of the reduced set of risk factor variables for evaluation by the machine learning classifier;
a model performance section that indicates performance characteristics of the machine learning classifier in evaluating the parameter values; or
a prediction probability section that provides a prediction probability indicator that indicates whether the patient is likely to encounter the health failure based on the evaluation by the machine learning classifier.

21. A method comprising:
identifying minority class data and majority class data in patient-level data, wherein the minority class data corresponds to patients with a health failure and the majority class data corresponds to patients without the health failure;
oversampling the minority class data to obtain synthetic class data; and
automatically reducing, via a machine learning classifier, risk factor variables to a reduced set of risk factor variables based on the majority class data, the minority class data and the synthetic class data, wherein the machine learning classifier includes an Extra Trees classifier configured to be trained by randomly sampling training data points when building a plurality of decision trees, considering random subsets of variables when splitting nodes of the plurality of decision trees, and testing random splits over a fraction of the variables.

22. A method comprising:
identifying minority class data and majority class data in patient-level data, wherein the minority class data corresponds to patients with a health failure and the majority class data corresponds to patients without the health failure;
oversampling the minority class data to obtain synthetic class data; and
automatically reducing, via a machine learning classifier, risk factor variables to a reduced set of risk factor variables based on the majority class data, the minority class data and the synthetic class data, wherein the machine learning classifier includes an Random Forest classifier configured to be trained by randomly sampling training data points when building a plurality of decision trees, considering random subsets of variables when splitting nodes of the plurality of decision trees, and testing all possible splits over a fraction of the variables.

23. A computing system comprising:
a processor; and a memory coupled to the processor, the memory including a set of instructions, which when executed by the processor, cause the computing system to:
- identify minority class data and majority class data in patient-level data, wherein the minority class data corresponds to patients with a health failure and the majority class data corresponds to patients without the health failure;
- oversample the minority class data to obtain synthetic class data; and
- automatically reduce, via a machine learning classifier, risk factor variables to a reduced set of risk factor variables based on the majority class data, the minority class data and the synthetic class data, wherein the machine learning classifier includes a Random Forest classifier configured to be trained by randomly sampling training data points when building a plurality of decision trees, considering random subsets of variables when splitting nodes of the plurality of decision trees, and testing all possible splits over a fraction of the variables.

\* \* \* \* \*

UNITED STATES PATENT AND TRADEMARK OFFICE
CERTIFICATE OF CORRECTION

PATENT NO.         : 11,996,201 B2
APPLICATION NO.    : 17/192237
DATED              : May 28, 2024
INVENTOR(S)        : Ediebah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 309 days.

Signed and Sealed this
Eighth Day of October, 2024

Katherine Kelly Vidal
*Director of the United States Patent and Trademark Office*